(12) United States Patent
Dimmer et al.

(10) Patent No.: US 8,020,227 B2
(45) Date of Patent: Sep. 20, 2011

(54) PATIENT SUPPORT SYSTEMS FOR USE WITH RADIATION THERAPY SYSTEMS AND OTHER APPLICATIONS

(75) Inventors: Steven C. Dimmer, Bellevue, WA (US); Matthew A. Herron, Palo Alto, CA (US); Edward J. Vertatschitsch, Bellevue, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 525 days.

(21) Appl. No.: 11/816,976

(22) PCT Filed: Oct. 18, 2004

(86) PCT No.: PCT/US2004/034523
§ 371 (c)(1),
(2), (4) Date: Nov. 14, 2008

(87) PCT Pub. No.: WO2005/037167
PCT Pub. Date: Apr. 28, 2005

(65) Prior Publication Data
US 2009/0211027 A1      Aug. 27, 2009

Related U.S. Application Data

(60) Provisional application No. 60/511,968, filed on Oct. 16, 2003.

(51) Int. Cl.
*A47B 13/00* (2006.01)
(52) U.S. Cl. ............................................ 5/601; 378/209
(58) Field of Classification Search .............. 5/601, 621, 5/600, 611–613, 632, 648; 378/209
See application file for complete search history.

(56) References Cited

U.S. PATENT DOCUMENTS

| | | | |
|---|---|---|---|
| 3,428,307 A | | 2/1969 | Hunter et al. |
| 3,897,345 A * | | 7/1975 | Foster ........................... 378/208 |
| 4,145,612 A * | | 3/1979 | Cooper .......................... 378/208 |
| 4,912,787 A * | | 4/1990 | Bradcovich ....................... 5/601 |
| 4,991,243 A * | | 2/1991 | Rottermann ...................... 5/600 |
| 5,537,454 A | | 7/1996 | Korver |
| 5,778,047 A * | | 7/1998 | Mansfield et al. ............ 378/209 |
| 5,950,627 A * | | 9/1999 | Bologovsky et al. .......... 128/869 |
| 6,161,237 A * | | 12/2000 | Tang et al. ........................ 5/621 |
| 6,260,220 B1 * | | 7/2001 | Lamb et al. ....................... 5/607 |
| 6,859,967 B2 * | | 3/2005 | Harrison et al. .................. 5/710 |

* cited by examiner

*Primary Examiner* — Robert G Santos
*Assistant Examiner* — Nicholas Polito

(57) ABSTRACT

An apparatus for supporting a patient in radiation therapy and other applications. In one embodiment, the apparatus includes a support structure and a panel carried by the support structure. The support structure can have first and second support members, such as rigid girders or other structures comprising substantially dielectric materials. The panel is also a rigid structure comprising substantially dielectric materials. The panels can further include a pass-through zone or other type of zone that is compatible with an ionizing radiation beam. For example, the panel can have a grid or solid low-density structure that mitigates beam contamination. The support structure and the panel together are configured to position a magnetic marker implanted in the patient in a navigational zone in which a magnetic field transmitted from the marker is not affected by conductive components or loops of conductive material in the pedestals or cantilevered support structures of conventional patient systems.

19 Claims, 8 Drawing Sheets

PATIENT SUPPORT SYSTEMS FOR USE WITH RADIATION THERAPY SYSTEMS AND OTHER APPLICATIONS

TECHNICAL FIELD

This application is related to patient support systems that are compatible with localizing systems for accurately locating and tracking a target in a body while it is being irradiated with an ionizing radiation beam.

BACKGROUND

Radiation therapy is currently used to treat localized cancer. In a typical application, a radiation delivery system has an ionizing radiation device mounted to a movable gantry. The radiation delivery system controls the motion of the radiation device to direct an ionizing radiation beam to a specific point in space commonly referred to as the "machine isocenter." One aspect of radiation therapy is positioning a patient so that the tumor is located at the machine isocenter. Calypso Medical Technologies, Inc. has developed systems and methods for accurately locating and tracking a target in a patient. The Calypso systems can provide objective information regarding the location of the tumor relative to the machine isocenter during patient setup procedures or while the ionizing radiation beam is irradiating the patient in real time (e.g., in less than 2 seconds from taking a measurement and in intervals of less than every 5 seconds).

One challenge of locating and tracking a tumor within a patient while the ionizing radiation beam is energized is that the tumor may move. Common sources of tumor movement during treatment include respiration, gastrointestinal functions, and muscular movement. The localizing and tracking systems developed by Calypso Medical Technologies, Inc. track the tumor or other target of the patient to ensure that the tumor is located at a desired position relative to the machine isocenter. The localizing and tracking system accordingly needs to provide accurate data to mitigate irradiating healthy tissue adjacent to the target.

One aspect of localizing a tumor is that conventional patient support systems for use in radiation therapy can impair the accuracy of the localization systems. Conventional patient support systems typically have a pedestal, a cantilevered support structure attached to the pedestal, and an insert carried by the cantilevered support structure. The insert generally includes a pass-through zone having a carbon fiber grid, and the cantilevered support structure generally has two beams that support the insert. The grid is designed to be compatible with the ionizing radiation beam and to provide sufficient support to sustain the load of the patient. Several different support systems and inserts are described in U.S. Pat. Nos. 5,778,047; 5,806,116; 5,537,454; and 6,161,237, all of which are herein incorporated by reference. Although the conventional patient support systems described in these patents are compatible with the ionizing radiation beams, they are not well suited for use with localizing and tracking systems that use magnetic fields or other types of signals to track the tumor.

Conventional patient support systems for use in other applications can also impair the accuracy of localization systems. For example, the localizing and tracking systems developed by Calypso Medical Technologies, Inc. can track tumors or other targets in a patient for surgical procedures, monitoring patients and diagnostic applications. Conventional patient support systems for these other applications can also impair the accuracy of the localization and tracking systems. Therefore, although conventional patient support systems for surgical procedures or other applications may be useful, they too are not well suited for use with localizing and tracking systems that use magnetic fields or other types of signals to track a target of a patient.

DETAILED DESCRIPTION

Figure 1:
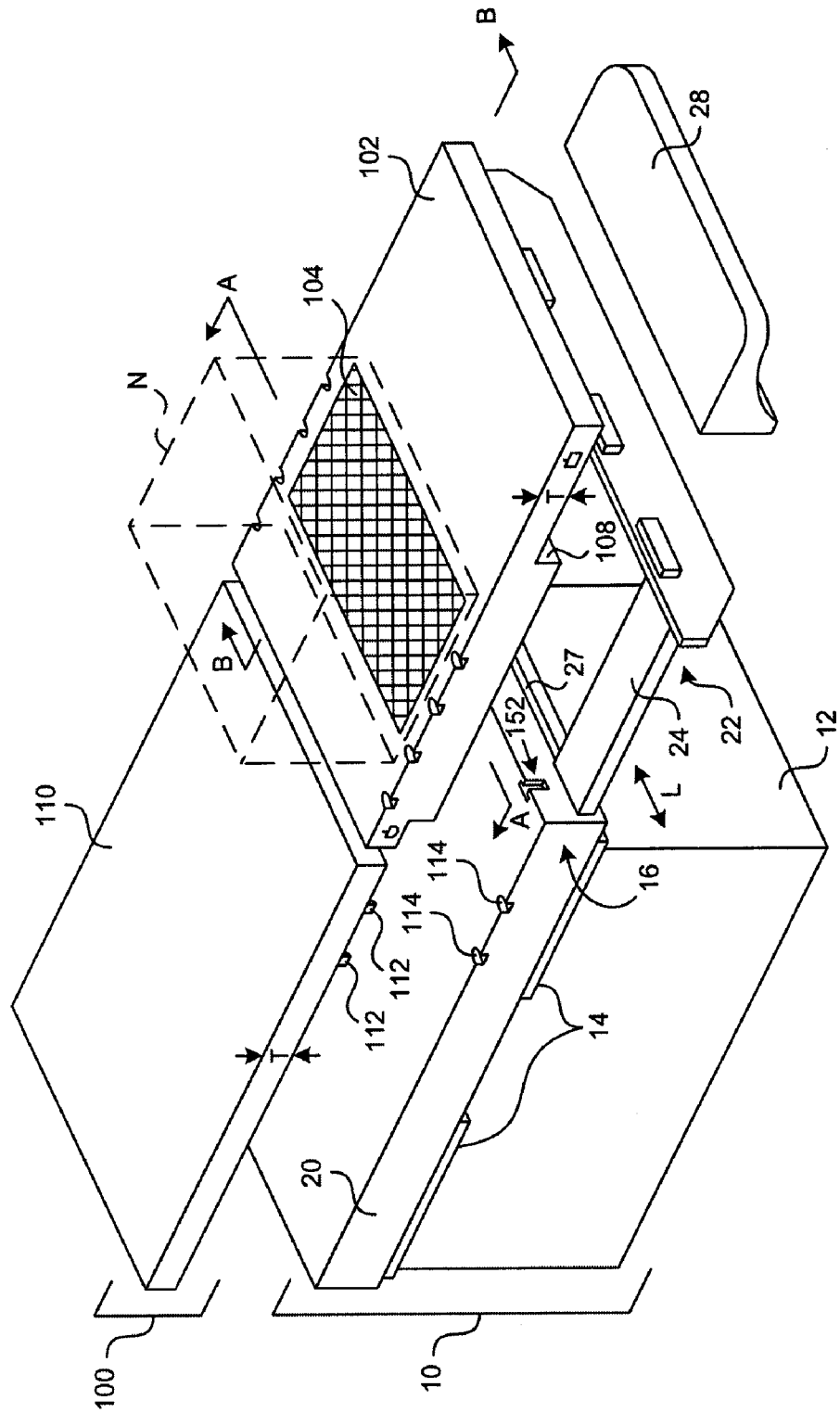
FIG. 1 is an exploded isometric view of a patient support system in accordance with an embodiment of the invention.

The following description describes several embodiments of patient support systems that are compatible with locating and tracking systems used in radiation therapy procedures, imaging procedures, surgical procedures, monitoring patients and/or other applications. The patent support systems can be used in applications involving ionizing radiation or in applications that do not involve ionizing radiation (e.g., surgery). Several embodiments of the patient support systems increase the accuracy of localizing systems that use an implantable marker that emits a magnetic field in response to an excitation field.

Several embodiments of the invention are directed toward an apparatus for modifying a conventional patient support system to be compatible with a magnetic field used for localization (e.g., a magnetic field generated by an implanted marker). The apparatus can be an overlay that rests on top of a conventional table or an insert for use with a conventional table. In one embodiment, the apparatus includes a support structure and a panel carried by the support structure. The support structure can have first and second support members, such as rigid girders or other structures comprising substantially dielectric materials. The panel is also a rigid structure comprising substantially dielectric materials. The panel can further include a pass-through zone or other type of zone that is compatible with an ionizing radiation beam. For example, the panel can have a grid or solid low-density structure that mitigates beam contamination. The support structure and the panel together are configured to position a magnetic marker implanted in the patient in a navigational zone in which a magnetic field transmitted from the marker is not affected by conductive components or loops of conductive material in the pedestals or cantilevered support structures of conventional patient support systems.

Another embodiment of the invention is directed toward a patient support system for use in treating a patient with an ionizing radiation beam or other non-ionizing procedures. The patient support system can include a pedestal and a cantilevered support structure. The cantilevered support structure can have a fixture attached to the pedestal and a plurality of beams projecting from the fixture. The patient support system can also include a platform that has a lower body section carried by the fixture and a torso section carried by the beams of the cantilevered support structure. The torso section comprises a substantially dielectric first girder, a substantially dielectric second girder, and a substantially dielectric panel carried by the first and second girders.

In operation, the region of the patient in which the marker is implanted is supported by components comprising substantially dielectric materials. Suitable substantially dielectric materials can have some conductivity, but the conductivity of these materials is less than that of carbon fiber composites. For example, suitable materials that are at least substantially dielectric include phenolic materials, foams, KEVLAR®, i.e., para-aramid synthetic fiber, fiberglass, etc.

Several embodiments of patient support systems and apparatus for modifying conventional patient support systems in accordance with the invention are set forth in FIGS. 1-5 and the corresponding text to provide a thorough understanding of particular embodiments of the invention. A person skilled in the art will understand, however, that the invention may have additional embodiments or that the invention may be practiced without several of the details of the embodiments shown in FIGS. 1-5. Additionally, suitable systems for locating and tracking the target are disclosed in the following U.S. application Ser. Nos., all of which are incorporated by reference in their entirety; Ser. Nos. 09/877,498; 10/334,700; 09/954,700; 10/027,675; 10/044,056; 10/213,980; 10/679,801; 10/382,123; and 10/334,698.

FIG. 1 is an exploded isometric view illustrating a base assembly 10 and a conversion apparatus 100 configured to be mounted to the base assembly 10. The conversion apparatus 100 supports a patient in a manner that is compatible with a magnetic field emitted by a magnetic marker implanted in the patient. The base assembly 10 includes a pedestal 12, a metal mounting structure 14, and a cantilevered support structure 16. The cantilevered support structure 16 includes a lower body section 20 attached to the metal mounting structure 14 and a free section 22 projecting from the lower body section 20. The free section 22 includes a plurality of beams 24 (only one shown in FIG. 1) and a head plate 26 attached to the beams 24. The beams 24 can be fixed to the lower body section 20, or the lower body section 20 can include a rail 27 along which the beams can move laterally (arrow L). The base assembly 10 further includes a headrest 28 that can be attached to the head plate 26.

The base assembly 10 in this embodiment can be similar to a conventional base assembly in which the components are made from metals or other materials without concern as to the conductivity of the materials. In a conventional application, a carbon fiber insert would be positioned over the beams 24 on the free section 22 of the cantilevered support structure 16. In this embodiment, however, a carbon fiber insert is not used.

The conversion apparatus 100 modifies the base assembly 10 so that it is suitable for use with implanted magnetic markers that emit a magnetic field to locate and track a tumor in the patient. In this embodiment, the conversion apparatus 100 is configured to position the patient relative to the base assembly 10 so that metal components or conductive loops of the base assembly 10 do not adversely affect the magnetic field emitted by a magnetic marker implanted in the patient. More specifically, the conversion apparatus 100 has a thickness T that raises the patient above the base assembly 10 by a distance that decreases the effect of the metal components in the base assembly 10 on a magnetic field generated by such an implanted magnetic marker. As explained in more detail below, the conversion apparatus 100 can also position the patient further out over the free section 22 of the cantilevered support structure 16 to further distance the marker implanted in the patient from metal in the base assembly 10.

The conversion apparatus 100 can include a torso section 102 having a pass-through zone 104 configured to be compatible with an ionizing radiation beam, and a plurality of indexing elements 106 for attaching peripheral devices to the torso section 102. The torso section 102 further includes a footing 108 configured to engage the cantilevered support structure 16 in a manner that replaces an insert that would otherwise be placed at the free section 22. The conversion apparatus 100 can further include a lower body section 110 that rests on the lower body section 20. The lower body section 110 can include tabs 112 configured to be received in recesses 114 in the lower body section 20 to align the two lower body sections 110 and 20 with each other.

Figure 2A:
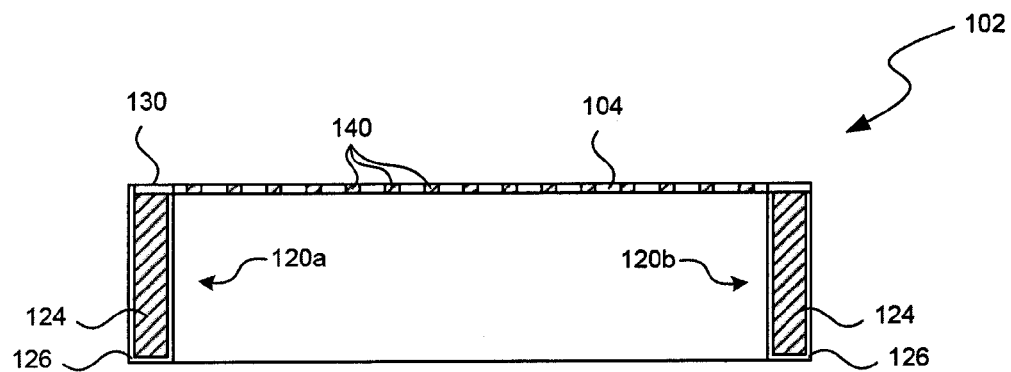
FIG. 2A is a cross-sectional view of a portion of the patient support system of FIG. 1 taken along section A-A.
Figure 2B:
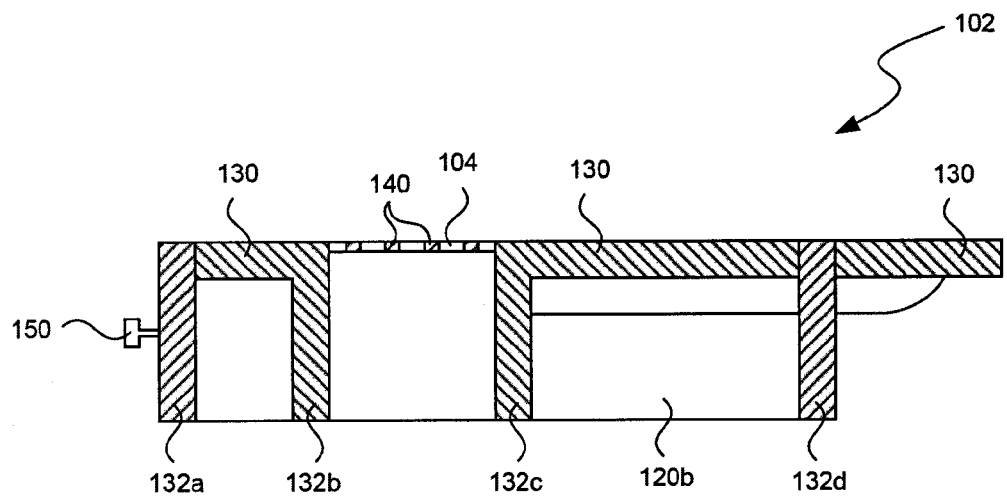
FIG. 2B is a cross-sectional view of a portion of the patient support system of FIG. 1 taken along section B-B.

FIG. 2A is a cross-sectional view of the torso section 102 taken along section A-A in FIG. 1, and FIG. 2B is a cross-sectional view of the torso section 102 taken along section B-B of FIG. 1. In this embodiment of the conversion apparatus 100, the torso section 102 includes at least a first girder 120a and a second girder 120b. The first and second girders 120a-b are longitudinal support members that extend in the direction of the beams 24 (FIG. 1). The first and second girders 120a-b can each include a core 124 and a covering 126. The core can be a foam, a honeycomb, or another suitable material that is at least substantially dielectric. In certain embodiments, the core 124 can be a phenolic material, but this material may not be used in the area of the pass-through zone 104 because it has a relatively high density. The covering 126 can include, among other materials, one or more sheets of KEVLAR®, para-aramid synthetic fiber, fiberglass, or other dielectric material. The covering 126 is typically laminated to the core 124 using a resin with a hardener or other suitable bonding material.

The torso section 102 further includes a panel 130 and a plurality of transverse girders 132a-d (best shown in FIG. 2B). The panel 130 can include a core having a covering of the same materials as the girders 120a-b. Additionally, the girders 132a and 132d can be formed of one type of material and the girders 132b-c can be formed of a different type of material. The girders 132a and 132d, for example, can be formed of a phenolic material covered by a covering, and the girders 132b-c can be formed from a foam or honeycomb that is covered by a covering. Certain sections of the panel 130 can be formed integrally with the transverse girders.

The pass-through zone 104 provides a low-density area that does not affect the ionizing radiation beam. The panel section 104 can be a rigid grid having a plurality of cross members 140. In one embodiment, the cross members 140 are formed from laminated layers of KEVLAR®, para-aramid synthetic fiber, and/or fiberglass. As explained in more detail below, the pass-through zone can have other low-density configurations compatible with an ionizing radiation beam, such as low-density panels instead of a mesh.

Referring to FIG. 2B, the torso section 102 further includes an attachment element 150 that can be received in a channel 152 (FIG. 1) of the lower body section 20 (FIG. 1). The attachment element 150 has a head and a stem that are received in corresponding structures of the channel 152 to hold the torso section 102 to the cantilevered support structure 16 (FIG. 1). The torso section 102 can be attached to the lower body section 20 using different systems with different attachment mechanisms.

The conversion apparatus 100 replaces a conventional insert to modify a conventional patient support system with metal components and/or conductive loops that would adversely affect a signal from a marker implanted in and/or on the patient. As such, conventional patient support systems can be converted to be compatible for use with a localizing system that computes the location of a magnetic marker implanted within the patient based on the magnetic field of the marker. One aspect of the conversion apparatus 100 is that it raises the patient above the base assembly 10 by the thickness T of the torso section 102 and the lower body section 110. Additionally the torso section 102 can space the pass-through section 104 longitudinally away from the pedestal 12 to further increase the distance between a marker implanted in the patient near the tumor and the metal components of the base assembly 10. In one application, the conversion apparatus raises the patient by approximately 7 cm and spaces the patient further apart from the base assembly longitudinally by approximately 7 cm. In so doing, the conversion apparatus 100 provides a navigational volume N in which a marker implanted in the patient can operate without being affected by metal components or conductive loops in the base assembly 10 to an extent that the accuracy of the location system is not within specification.

Several embodiments of the conversion apparatus 100 further combine the non-conductive aspects of the device and the low-density pass-through zone for use in radiation therapy. The dielectric qualities of the apparatus mitigate or eliminate inaccuracies caused by conductive materials or conductive loops of the base support assembly, and the low-density pass-through zone mitigates contamination of the high-intensity ionizing radiation beam. As such, several of the embodiments shown and described with reference to FIGS. 1-2B are well suited for use with non-ionizing localization systems and radiation treatment equipment.

Figure 3:
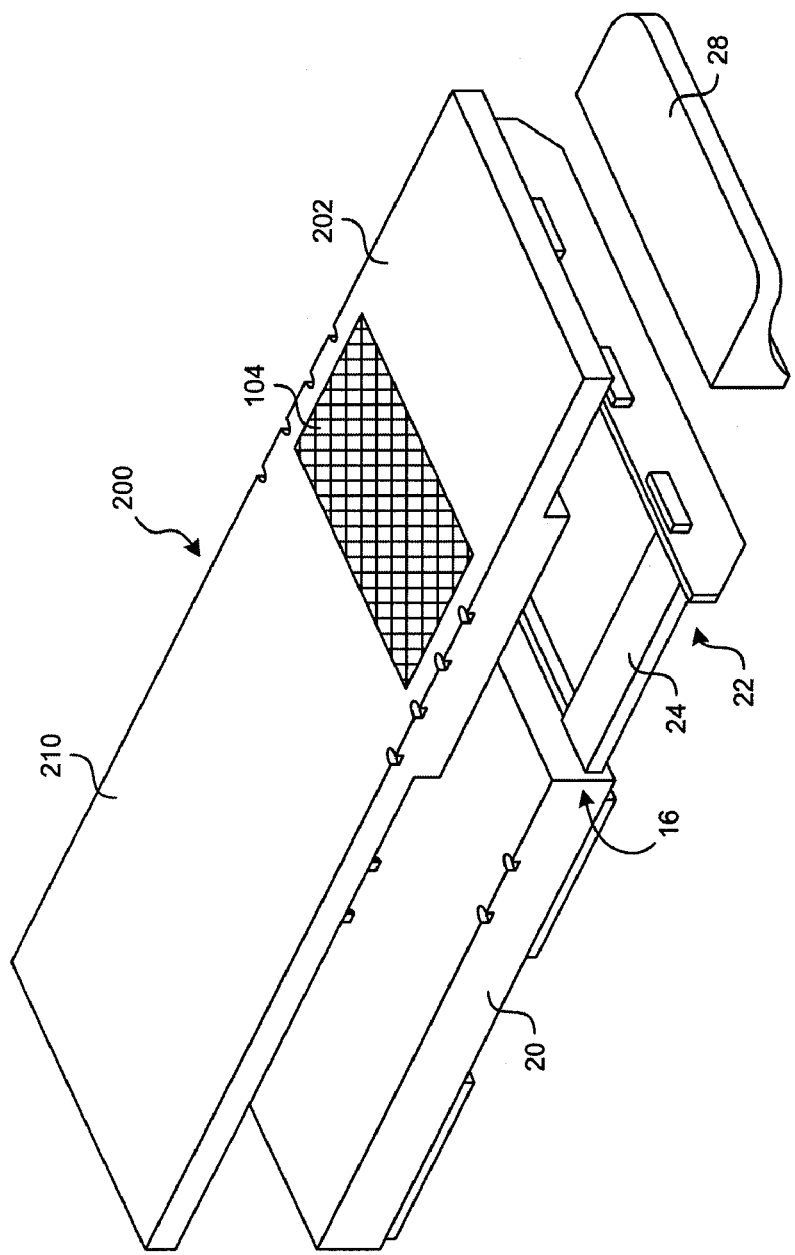
FIG. 3 is an exploded isometric view illustrating a patient support system in accordance with another embodiment of the invention.

FIG. 3 is an exploded isometric view of a patient support system in accordance with another embodiment of the invention. In this embodiment, the patient support system includes a conversion apparatus 200 having a torso section 202 and a lower body section 210 that are integral with each other. The conversion apparatus 200 is expected to operate similarly to the conversion apparatus 100 described above with respect to FIGS. 1-2B.

Figure 4:
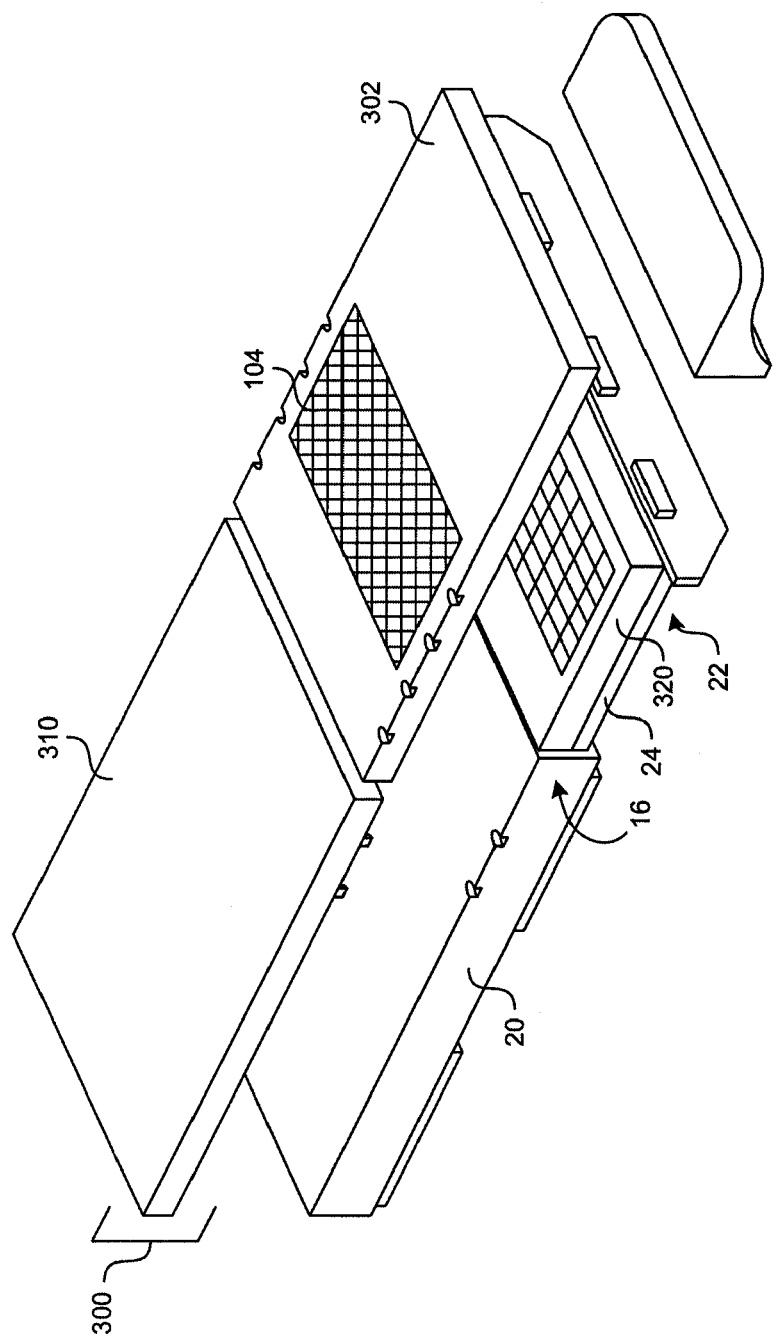
FIG. 4 is an isometric view of a patient support system in accordance with yet another embodiment of the invention.

FIG. 4 is an exploded isometric view of a conversion apparatus 300 in accordance with another embodiment of the invention. In this embodiment, the conversion apparatus 300 has a torso section 302 and a lower body section 310. The conversion apparatus 300 is different than the conversion apparatus 100 in that the torso section 302 is configured to be used in a system in which a conventional insert 320 is mounted to the cantilevered support structure 16. The torso section 302 accordingly does not have the footing 108 (FIG. 1) of the conversion unit 100.

Figure 5:
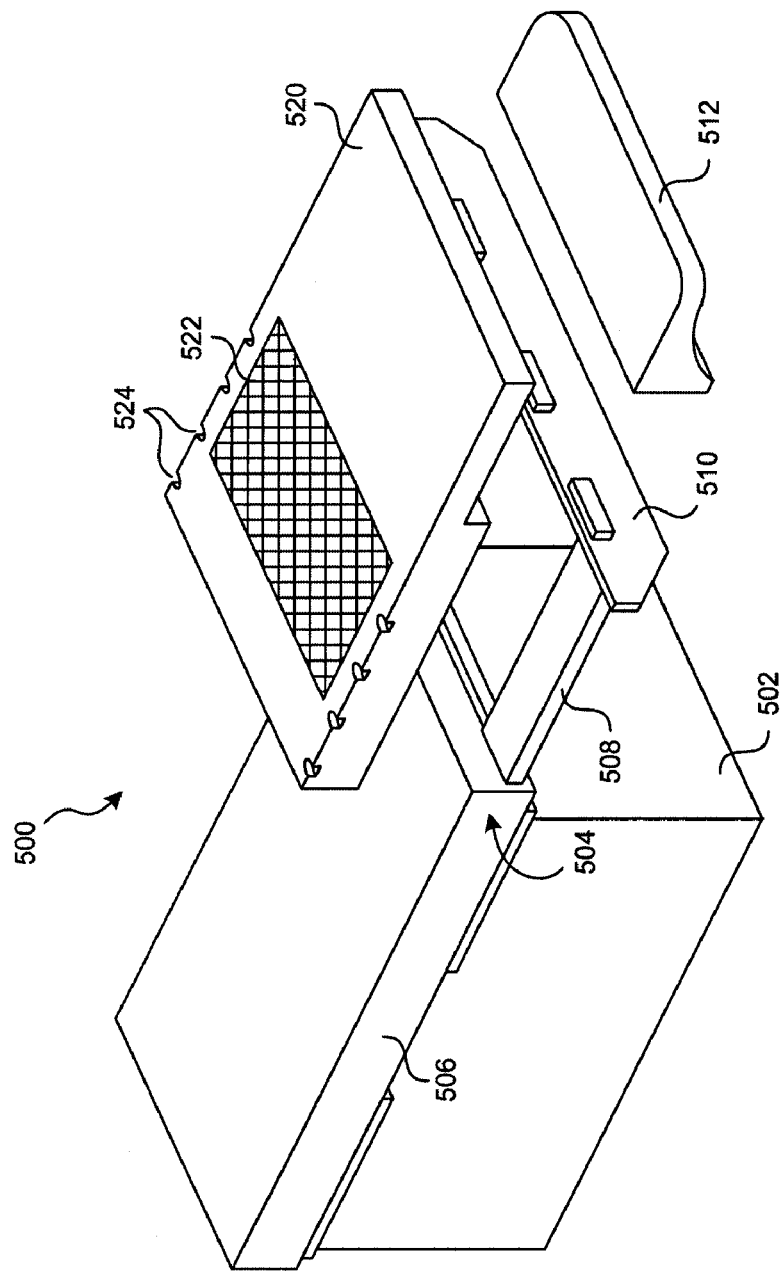
FIG. 5 is an exploded isometric view of a patient support system in accordance with still another embodiment of the invention.

FIG. 5 is an exploded isometric view of a patient support system 500 that is compatible for use with a localization system having an implanted magnetic marker that emits a magnetic field. The patient support system 500 can include a base 502 and a cantilevered support structure 504 having a lower body section 506 attached to the base 502 and beams 508 projecting from the lower body section 506 (only one beam 508 shown in FIG. 5). The base 502 and the cantilevered support structure 504 can be similar to the same elements described above, but the base 502 and the cantilevered support structure 504 can include components composed, at least in part, of materials that are at least substantially dielectric. The base 502 can also have fewer conductive loops than conventional equivalent components. For example, the lower body support section 506 and the beams 508 can comprise substantially dielectric materials similar to the structures described above. The patient support system 500 further includes an insert 520 having a pass-through section 522. The insert 520 can be similar to the torso section 102 described above with respect to FIG. 1. The insert 520 can accordingly include a plurality of index elements 524.

Figure 6:
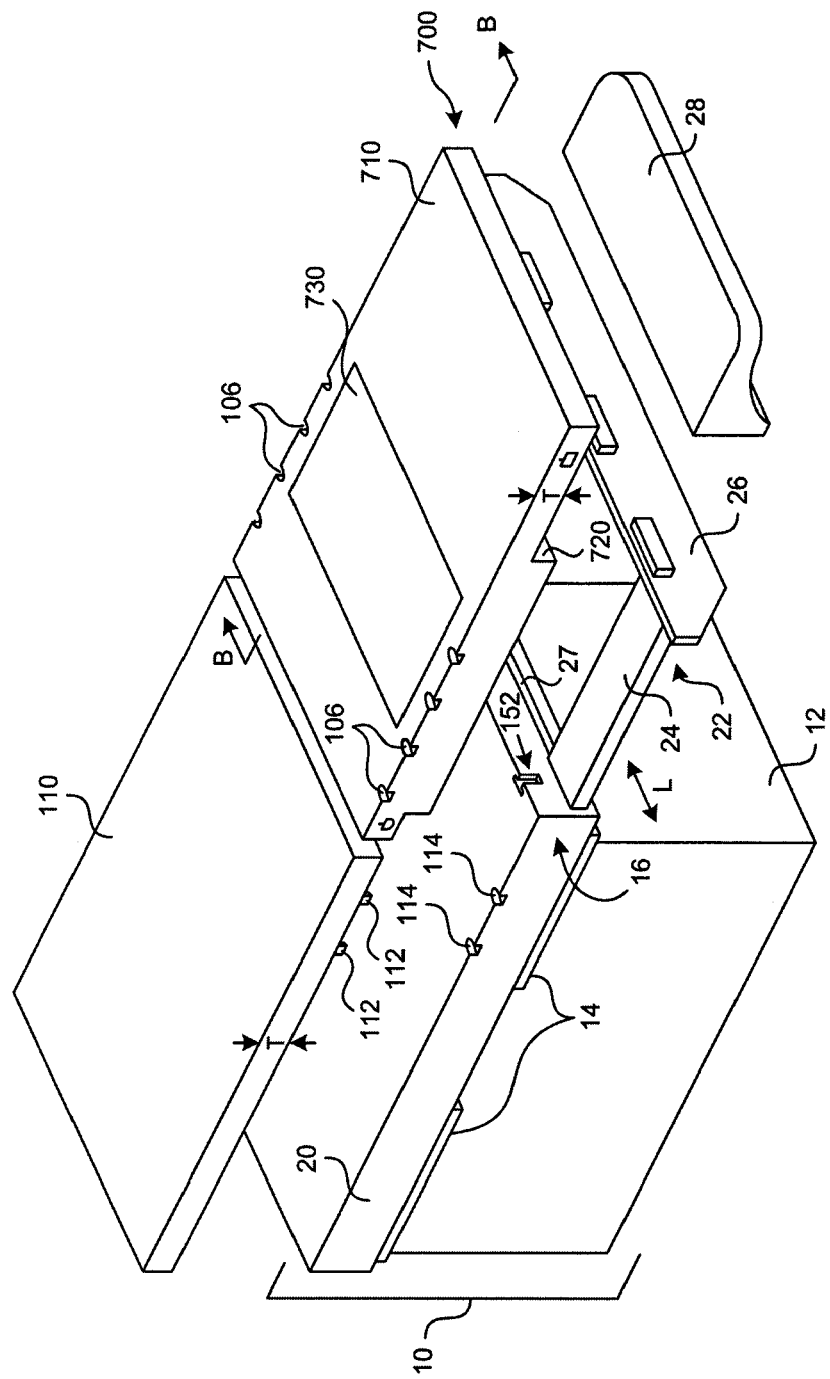
FIG. 6 is an exploded isometric view of a patient support system in accordance with another embodiment of the invention.
Figure 7:
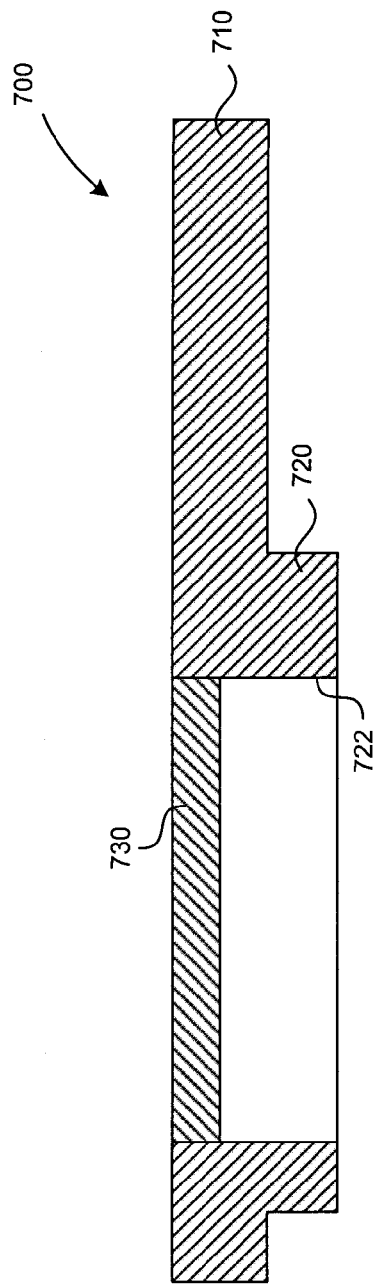
FIG. 7 is a cross-sectional view of a portion of the patient support system of FIG. 6 taken along section 7-7.

FIG. 6 is an isometric view illustrating an apparatus 700 for modifying a patient support for use with a localization system in accordance with another embodiment of the invention, and FIG. 7 is a cross-sectional view of the apparatus 700 taken along section 7-7. Several features of the apparatus 700 are similar to the apparatus 100 described above with reference to FIGS. 1-2B. For example, the apparatus 700 has a torso section 710 with thickness T to raise a patient above the base support assembly 10 by a sufficient distance to mitigate the effect of the metal components in the base support assembly 10 on a magnetic field generated by an implantable magnetic marker used in the localization system. In this embodiment, the apparatus 700 further includes a footing 720 and an opening 722. It will be appreciated that the footing 720 is an optional feature for use when the apparatus 700 is attached to a cantilevered support structure as shown in FIG. 6. The torso section 710 and the footing 720 are composed of dielectric materials such as para-aramid synthetic fiber wrapped foam cores, plastics, high-density polypropylene, fiberglass wrapped cores, and other suitable materials.

The apparatus 700 further includes a pass-through zone 730 in the opening 722. The pass-through zone 730 in this embodiment comprises a panel of low-density material suitable for use with an ionizing radiation beam. The panel, for example, can be composed of a low-density foam wrapped with KEVLAR®, para-aramid synthetic fiber, fiberglass or other materials. The covering is generally laminated to the core using a resin and a hardener. The pass-through zone 730 can alternatively have a honeycomb core or other type of core composed of fiberglass, cellulose-based products, plastics, or other suitable materials that can adequately support a patient either alone or when wrapped with other materials. In one embodiment, the mass-density of the pass-through zone 730 is measured by the amount of mass in a square centimeter column through the thickness of the pass-through zone 730. The pass-through zone 730 is generally constructed to have a low mass-density to allow the pass-through zone 730 to dwell in the radiation beam during delivery of radiation therapy to a patient without excessive contaminating beam. In the illustrated embodiment, the mass-density of the pass-through zone 730 is in the range of approximately 1.0 grams/cm2 or less, such as approximately 0.3 grams/cm2 or less. The pass-through zone 730 should be configured to attenuate the radiation beam by approximately only 0.5% or less. In other embodiments, the pass-through zone 730 can have a different mass-density or attenuate the radiation beam by greater than 0.5%.

Figure 8:
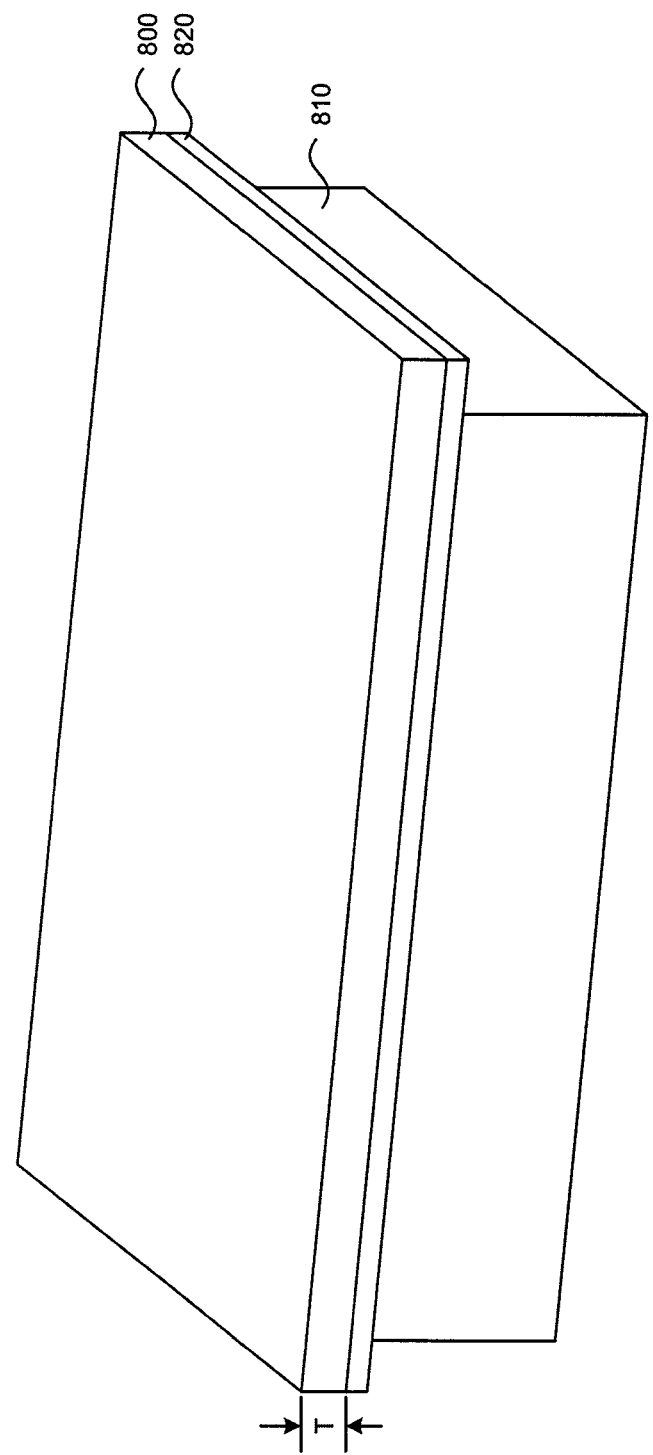
FIG. 8 is an isometric view of a patient support system in accordance with still another embodiment of the invention.

FIG. 8 is an isometric view illustrating another embodiment of an apparatus 800 for supporting a patient for use with localization and tracking systems. In this embodiment, the apparatus 800 is a dielectric tabletop attached to or otherwise supported by a base 810 and a panel 820. The apparatus 800 has a thickness T that spaces the patient apart from metal components in the base 810 and the panel 820. The apparatus 800 can be composed of a dielectric core wrapped with a suitable skin to provide a substantially rigid spacer on the panel 820. The core, for example, can be a closed-cell foam, honeycomb structure or other suitable dielectric material, and the skin can be one or more sheets of KEVLAR®, para-aramid synthetic fiber, fiberglass or other dielectric material. The skin or covering can be laminated to the core using a resin with a hardener or other suitable bonding material. In other embodiments, the apparatus 800 can be another dielectric structure having the requisite thickness T that does not have an outer covering wrapped around a core. The apparatus 800 is particularly suitable for surgical applications or other applications that do not necessarily require a low-density pass-through zone to accommodate a radiation beam used in radiation therapy.

From the foregoing, it will be appreciated that specific embodiments of the invention have been described herein for purposes of illustration, but that various modifications may be made without deviating from the spirit and scope of the invention. For example, the patient support systems can further include additional features such as attachment mounting elements that are configured to allow only accessories made from materials that are at least substantially dielectric to be attached to the conversion apparatus or the inserts. Additionally, other materials or dimensions can be used instead of those described above, and some of the components described above as being composed of substantially dielectric materials can include small features made from conductive materials for additional structural strength. The torso sections can also have other configurations as set forth above (e.g., a solid panel of low-density material without a grid). Accordingly, the invention is not limited by the foregoing description as exemplified by the following claims.

We claim:

1. In equipment for treating a target within a patient using an ionizing radiation beam, an apparatus for modifying a patient support system to be compatible with a magnetic field used for localization, comprising:
 a support structure having a first longitudinal support member and a second longitudinal support member, the first and second longitudinal support members being rigid and comprising materials that are at least substantially dielectric, and the first and second support members being configured to be carried by the patient support system;
 a panel carried by and positioned at a top of the first and second longitudinal support members, the panel comprising materials that are at least substantially dielectric and having a portion that is compatible with an ionizing radiation beam; and
 a pass-through zone positioned on the panel between the first and second longitudinal support members, the pass-through zone including a rigid grid having a plurality of cross members, not including a high density core, and the pass-through zone being configured to provide a navigational zone wherein a signal transmitted from a marker implanted in a patient in the navigational zone is not affected by conductive components of the patient support system to an unacceptable degree.

2. The apparatus of claim 1, wherein the first and second support members comprise first and second girders, respectively, composed of a thermosetting resin.

3. The apparatus of claim 1, wherein the first and second support members comprise first and second girders, respectively, composed of a phenolic material.

4. The apparatus of claim 1, wherein the first and second longitudinal support members comprise first and second longitudinal girders, respectively, and the support structure further comprises a transverse third girder extending between the first and second longitudinal girders.

5. The apparatus of claim 1, wherein the panel comprises a low-density core and a covering laminated on the core.

6. The apparatus of claim 5, wherein the covering comprises para-aramid synthetic fiber and/or fiberglass.

7. The apparatus of claim 5, wherein the covering comprises a dielectric sheet laminated to the core and the support structure with a resin.

8. The apparatus of claim 5, wherein the core comprises a dielectric foam and/or a dielectric honeycomb.

9. The apparatus of claim 5, wherein the covering comprises para-aramid synthetic fiber and/or fiberglass, and the core comprises a dielectric foam and/or a dielectric honeycomb.

10. The apparatus of claim 1, wherein the support structure and the panel space the navigational zone apart from a base by a sufficient distance to reduce errors induced by electrically conductive components of the patient support system.

11. The apparatus of claim 1, wherein the support structure and the panel comprise an overlay configured to be placed over an insert of the patient support system in a manner that raises the navigational zone.

12. The apparatus of claim 1, wherein the support structure and the panel comprise an overlay configured to be placed over rails of the patient support system without an insert between the support structure and the rails in a manner that raises the navigational zone.

13. The apparatus of claim 1, wherein the support structure and the panel comprise an insert configured to replace a conventional conductive insert of the patient support system.

14. The apparatus of claim 1, further comprising a reference system to locate accessories relative to the patient.

15. The apparatus of claim 1, further comprising selective attachment elements that allow only substantially dielectric accessories and side rails to be mounted to the patient support system.

16. The apparatus of claim 1, further comprising a lower body support structure.

17. The apparatus of claim 1, wherein the first and second longitudinal support members and the panel have a conductivity less than carbon-fiber.

18. An apparatus for modifying a patient support system to be compatible with a magnetic field used for localization during ionizing radiation, comprising:
 a support structure having a first longitudinal support member and a second longitudinal support member, the first and second longitudinal support members being rigid and comprising materials that are at least substantially dielectric, the first longitudinal support member spaced apart from and in a fixed relative position to the second longitudinal support member, and the first and second longitudinal support members being configured to be carried by the patient support system;
 a panel carried by the first and second longitudinal support members, the panel comprising materials that are at least substantially dielectric;
 a pass-through zone configured to be compatible with an ionizing radiation beam, the pass-through zone positioned on the panel between the first and second longitudinal support members and including a rigid grid having a plurality of cross members, not including a high density core; and
 the pass-through zone being configured to provide a navigational zone in which a signal transmitted from the marker implanted in a patient in the navigational zone is not affected by conductive components of the patient support system to an unacceptable degree.

19. An apparatus for modifying a patient support system to be compatible with a magnetic field used for localization, comprising:

a support structure having a first longitudinal support member and a second longitudinal support member, the first and second longitudinal support members being rigid, and comprising materials that are at least substantially dielectric, and the first and second longitudinal support members being configured to be carried by the patient support system;

a panel integrally connecting the first and second longitudinal support members, the panel comprising materials that are at least substantially dielectric and having a zone that is compatible with an ionizing radiation beam; and a pass-through zone positioned on the panel between the first and second longitudinal support members, the pass-through zone including a rigid grid having a plurality of cross members, not including a high density core, and the pass-through zone being configured provide a navigational zone wherein a signal transmitted from a marker implanted in a patient in the navigational zone is not affected by conductive components of the patient support system to an unacceptable degree.

* * * * *